(12) United States Patent
Suh (10) Patent No.: US 9,073,623 B1
(45) Date of Patent: Jul. 7, 2015

(54) SYSTEM AND METHOD FOR DYNAMIC AEROELASTIC CONTROL

(71) Applicant: The United States of America as Represented by the Administrator of NASA, Washington, DC (US)

(72) Inventor: Peter M. Suh, Tehachapi, CA (US)

(73) Assignee: The United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 14/207,757

(22) Filed: Mar. 13, 2014

Related U.S. Application Data

(60) Provisional application No. 61/798,078, filed on Mar. 15, 2013.

(51) Int. Cl.
| | |
|---|---|
| *G01C 23/00* | (2006.01) |
| *B64C 19/00* | (2006.01) |
| *G01N 21/00* | (2006.01) |
| *G10K 15/04* | (2006.01) |
| *G01J 1/04* | (2006.01) |
| *G01S 15/88* | (2006.01) |
| *B64C 25/20* | (2006.01) |
| *G03B 39/00* | (2006.01) |
| *G01M 3/04* | (2006.01) |
| *G01N 21/43* | (2006.01) |
| *G08G 5/06* | (2006.01) |
| *B64D 43/00* | (2006.01) |
| *B64D 47/00* | (2006.01) |

(52) U.S. Cl.
CPC ............... *B64C 19/00* (2013.01); *G01N 21/00* (2013.01); *G10K 15/04* (2013.01); *G01J 1/04* (2013.01); *G01S 15/88* (2013.01); *B64C 25/20* (2013.01); *G03B 39/00* (2013.01); *G01M 3/047* (2013.01); *G01N 21/431* (2013.01); *G08G 5/06* (2013.01); *B64D 43/00* (2013.01); *B64D 47/00* (2013.01)

(58) Field of Classification Search
CPC ......... G01J 1/04; G01N 21/00; G01N 21/431; G01M 3/047; B63H 1/06; B63H 1/00; G10K 15/04; G01S 15/88; G08G 5/06; B64D 47/00; B64D 43/00
See application file for complete search history.

(56) References Cited

U.S. PATENT DOCUMENTS

| | | | |
|---|---|---|---|
| 5,642,445 A * | 6/1997 | Bucaro et al. | 385/12 |
| 7,216,018 B2 | 5/2007 | Zuo et al. | |
| 7,222,027 B2 | 5/2007 | Gorinevsky et al. | |
| 7,645,970 B2 | 1/2010 | Adams et al. | |
| 2009/0204355 A1 | 8/2009 | Vold | |
| 2011/0042557 A1 * | 2/2011 | Mossman | 250/227.16 |

OTHER PUBLICATIONS

Shelley, S. J., Pickrel, C. R., "New Concepts for Flight Flutter Parameter Estimation," Proc. SPIE vol. 3089, p. 490, Proceedings of the 15th International Modal Analysis Conference.

(Continued)

*Primary Examiner* — Behrang Badii
(74) *Attorney, Agent, or Firm* — Mark Homer (57) ABSTRACT

The present invention proposes a hardware and software architecture for dynamic modal structural monitoring that uses a robust modal filter to monitor a potentially very large-scale array of sensors in real time, and tolerant of asymmetric sensor noise and sensor failures, to achieve aircraft performance optimization such as minimizing aircraft flutter, drag and maximizing fuel efficiency.

20 Claims, 5 Drawing Sheets

(56) References Cited

OTHER PUBLICATIONS

Cooper, J. E., "Towards Faster and Safer Flight Flutter Testing," 2003, Manchester Univ School of Engineering (UK) Defense Technical Information Center.

Lind, R., Brenner, J. J., "Robust flutter margin analysis that incorporates flight data", NASA Dryden Flight Research Center TP-1998-206543.

Jae-Hung Hana, Junji Tanib, Jinhao Qiub, "Active flutter suppression of a lifting surface using piezoelectric actuation and modern control theory," Journal of Sound and Vibration, vol. 291, Issues 3-5, Apr. 4, 2006, pp. 706-722 (Abstract).

Trindade, M.A., Pagani, C.C. Jr., Massaroppi, E. Jr., "Robustness of Modal Filters Using Piezoelectric Sensor Arrays Subject to Positioning Uncertainties," Mecanica Computacional vol. XXIX, pp. 6865-6881 (2010).

Freudinger, L. C., "Analysis of Structural Response Data Using Discrete Modal Filters," NASA Contractor Report 179448, 1991.

Advanced Frequency-Domain Modal Analysis for Dealing with Measurement Noise and Parameter Uncertainty, Topics in Modal Analysis 1, vol. 5—Conference Proceedings of the Society for Experimental Mechanics Series vol. 30, 2012, pp. 179-199 (Abstract).

Schultze, J. F., Rost, R. W., Shelley, S. J., "Adaptive Modal Space Control of Flexible Structures Theory."

Schultze, J. F., Rost, R. W., Shelley, S. J., "Adaptive Modal Space Control of Flexible Structures Applications" IMAC XV—15th International Modal Analysis Conference, 1997.

Yeon Kim, Kim Ryeol, Kwang-Joon, "Indirect input identification by modal model technique," Mechanical Systems and Signal Processing vol. 13, Issue: 6, pp. 893-910, 1999.

Matsumura, Y. Hsoya, N., "Spatial Filter Design for Observation Spillover Suppression," Journal of Environment and Engineering, vol. 2, No. 3, 2007.

Cohen, D.E., "Trim Angle of Attack of Flexible Wings Using Non-Linear Aerodynamics," 7th AIAA/USAF/NASA/ISSMO Symposium on Multidisciplinary Analysis and Optimization, 1998.

Silva, Walter A., "Development of Reduced Order Models for Aeroelastic Analysis and Flutter Prediction Using the CFL3Dv6.0 Code" American Institute of Aeronautics and Astronautics, 2002.

Rodrigues, Eduardo A. et al., "Computation on Dynamic Loads on Aircraft Structure Due to Continuous Gust Using MSC/NASTRAN", The MacNeil-Schwendler Corporation, 1997.

\* cited by examiner

SYSTEM AND METHOD FOR DYNAMIC AEROELASTIC CONTROL

CROSS-REFERENCE TO RELATED APPLICATION(S)

The present application derives priority from U.S. provisional application Nos. 61/798,078 filed 15 Mar. 2013 and 61/905,698 filed Nov. 18, 2013.

STATEMENT OF GOVERNMENT INTEREST

The invention described hereunder was made in the performance of work under a NASA contract, and is subject to the provisions of Public Law #96-517 (35 U.S.C. 202) in which the Contractor has elected not to retain title.

BACKGROUND a. Field of Invention

The invention relates to structural monitoring and, more particularly, to a hardware and software architecture for dynamic modal structural monitoring and control that monitors the dynamics of a structure such as an aircraft in the presence of complex loading patterns using a robust modal filtering architecture, with integrated distributed shape and accelerometer sensing.

b. Background of the Invention

Monitoring the states of a structure is useful for safety, control and performance optimization in a wide variety of applications. For example, fuel efficiency and safety are of paramount importance to the aviation industry. Toward this end, lightweight composite material use in aircraft is now a common practice. However, increased flexibility leads to an aircraft which is more susceptible to dynamic phenomena such as gusts, flutter, and buffeting, which negatively affect safety and performance and can be potentially destructive. Consequently, demand has grown in the aviation industry for aircraft that are capable of monitoring and managing such dynamics. Typical aeroelastic control methods identify optimal control surface settings for minimum drag from indirect sensory data such as wing root load balances, engine RPM or thrust/fuel, but such parameters do not give an accurate reflection of the true structural state of an aircraft.

Several approaches have been proposed for more reliable real-time estimation of structural states. However most are frequency based methods which utilize conventional sensors to monitor a structure's natural frequency response. These methods are suitable for single-mode vibration suppression, but have limited effectiveness for the multi-mode vibration suppression. Flexible aircraft are highly complex structures with multiple vibration modes, and active control of such large flexible structures is more readily achieved with multiple input multiple output (MIMO) control algorithms.

An estimator which supports a MIMO type control algorithm is the spatial filter or modal filter. Modal filtering is a known spatial filtering technique which transforms physical coordinates to modal coordinates. The modal coordinates can be used to capture the contribution of both static and dynamic deformation in the structure. Modal filtering methods are generally well known in the art and are disclosed in numerous publications including Shelley, S. J., Investigation of Discrete Modal Filters for Structural Dynamics Applications, Department of Mechanical and Industrial Engineering, University of Cincinnati, 1990. Discrete/continuous modal filters and dynamic state estimators have typically been used for sensing modal coordinates in trusses and bridges.

A pseudo inverse modal filter, developed by Zhang, was implemented by Shelley et al. on a five meter truss structure, showing promise for real-time monitoring of the structure. Shelley, S., Freudinger, L, Allemang, R. J., and Zhang, Q. "Implementation of a Modal Filter on a Five Meter Truss Structure." IMAC IX Conference, Florence Italy, Proceeding Volume 2. p. 1036-1044. Unfortunately the pseudo-inverse modal filter is not fault-tolerant and fails as soon as one sensor fails.

Shelley et al. later proposed an adaptive modal filter technique to compensate for small sensor failure or calibration drift. Shelley, S. J., Allemang, R. J., Slater, G. L., Shultze, J. F., Active Vibration Control Utilizing an Adaptive Modal Filter Based Modal Control Method, 11$^{th}$ International Modal Analysis Conference, Kissimmee, Fla., Feb. 1-4, 1993. However, the Shelley et al. adaptive modal filter must be programmed with the natural frequency, modal damping, and modal residue of the structure. While these parameters can be initially calculated, they will tend to drift over time. Shelly's algorithm is also based upon least mean squares (LMS), which has similarly bad resistance to gross outliers (large sensor bias) as least squares. In flight, the strain can be very high. If a sensor failure occurs and the sensor reading is near zero while the rest are at normal values, the sensor reading near zero is characterized as a gross outlier. This could completely bias a modal filter estimate using either least mean squares or ordinary least squares.

Nevertheless, if these past deficits can be overcome the modal filter has the potential to benefit the aerospace field significantly. What is needed is a system and method for dynamic modal structural monitoring and control that integrates a very large-scale array of sensors including distributed strain and acceleration sensing for the purposes of robust modal filtering (in lieu of the pseudo-inverse modal filter), in real time, while being completely tolerant to multiple sensor failures and asymmetric sensor error.

The present invention provides such a system, and in so doing offers more reliable estimates of the modal displacements and velocities for flexible aircraft structural feedback control than the current state of the art, especially in the presence of uncertainty and multiple sensor failures.

SUMMARY OF THE INVENTION

It is, therefore, an object of the present invention to provide a robust and fault-tolerant system for dynamic modal structural monitoring and control.

It is another object to provide a method and system for improved aeroelastic control suitable for flight safety critical aircraft operation.

It is another object to implement a real time spatial modal filtering system in a robust manner that is insensitive to asymmetric sensor noise and sensor failures.

It is yet another object to implement a practical aeroelastic control (where modal frequencies and modal shapes change with air speed) that employs real time spatial modal filtering for active flutter suppression (AFS), aircraft performance improvement, and loads alleviation.

According to the present invention, the above-described and other objects are accomplished by providing a hardware and software architecture for dynamic modal structural monitoring that uses a robust modal filter to monitor a potentially very large-scale array of sensors in real time, and tolerant of asymmetric sensor noise and sensor failures, to achieve aircraft performance optimization such as suppressing aircraft flutter, minimizing drag and maximizing fuel efficiency.

BRIEF DESCRIPTION OF THE DRAWINGS

Additional aspects of the present invention will become evident upon reviewing the embodiments described in the specification and the claims taken in conjunction with the accompanying figures, wherein like numerals designate like elements, and wherein:

DETAILED DESCRIPTION OF THE PREFERRED EMBODIMENT

The present invention is a hardware and software architecture for dynamic modal structural monitoring that integrates modal filtering, to monitor an array of sensors using a robust modal filter, in real time, immune to asymmetric sensor noise and sensor failures. The invention provides a practical, real-time approach to monitor the complex dynamics of a flexible aircraft using a robust modal filtering algorithm based on the hybridization of a computationally efficient concentration-based estimator and M-estimation.

Overview

Figure 1:
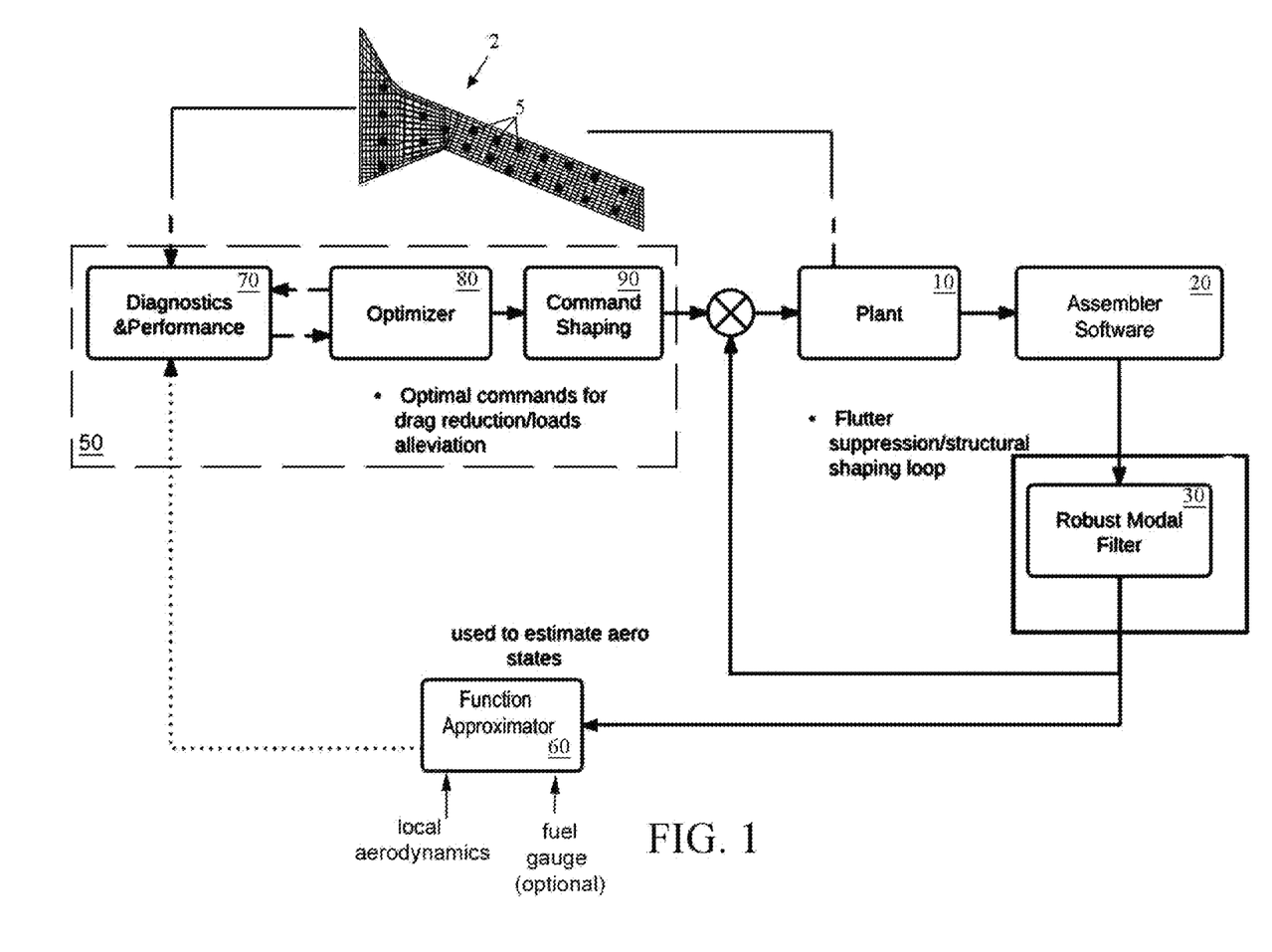
FIG. 1 is a block diagram of an embodiment of the present system architecture for aeroelastic control and aerodynamic optimization.

An embodiment of the present system architecture for aeroelastic control is shown in FIG. 1. The plant 10 is a mathematical model used to represent the aircraft to be controlled, which in this case is illustrated as a wing model. The wing is equipped with a sensor array 2 for measuring shape (deflection or strain) at multiple locations on the wing structure.

Sensor array 2 preferably comprises a fiber-optic sensor (FOSS) array 2 which is used to measure strain or shape. The individual sensors 5 in array 2 can be used by way of modal filtering to determine the modal displacement states of aeroservoelastic state-space models. A distributed array of Fiber Bragg Grating sensors is well-suited as FOSS array 2, as explained in B. Childers et al., "Use Of 3000 Bragg Grating Strain Sensors Distributed On Four Eight-Meter Optical Fibers During Static Load Tests Of A Composite Structure," Proc. of SPIE, 4332, 133-142 (2001). FOSS array 2 includes numerous FBG sensors, placed at regular intervals along multi-core (three or more channels in a single fiber) optical fibers. A multi-core FOSS array 2 is able to capture deformation (x,y,z) from its un-deflected position in real time with good accuracy, without any knowledge whatsoever of the structure to which it is adhered to. The strain measurements from each fiber core indicate the direction and amount of bend in the fiber. The amount of strain in each core is proportional to the bend radius and to the position of each core relative to the bend. Alternatively, FOSS array 2 may employ a photogrammetric technique to measure shape at all (x,y,z) locations.

The aircraft carries a computerized feedback loop capable of executing the various feedback software modules 10, 20, 30, 40 of the present invention, including plant model 10, modal filter assembler software 20, robust modal filter 30, and function approximator 60. Suitable computing devices include a processor, memory (e.g. RAM), a bus which couples the processor and the memory, a mass storage device (e.g. a magnetic hard disk or an optical storage disk) coupled to the processor and the memory through an I/O controller. It is envisioned that at least a 2.8 GHz processor will suffice to provide the necessary computation rate of 1,830 Hzm for real-time operation though parallel processing may be preferred in some cases. The aircraft also carries a flight controller 50 which also has various control software modules 60, 70, 80 for developing and executing the various aeroeleastic control commands as a result of the feedback software 10, 20, 30, 40.

The modal filter assembler software 20 described herein computes the components necessary for the robust modal filter 30. Assembler software 20 comprises either of two variations. If strain measurements exist in Sensor array 2, then the strain is computed at each (x,y,z) location of the FBG sensors in real time. Assembler software 20 also assembles the strain mode matrix corresponding to the same (x,y,z) locations. The measurements and strain mode matrix are passed to the robust modal filter 30. Note that the strain mode matrix must only be computed once.

The second variation of software 20 is provided when shape at all (x,y,z) locations is estimated from a measurement technique such as photogrammetry in real time. During processing of Assembler software 20 the shape modal matrix is computed at the same (x,y,z) locations. The measurements and shape modal matrix are passed to the robust modal filter 30. Again, the shape modal matrix must only be computed once.

Getting these distributed measurements and a modal matrix (either shape or strain as per above) is all that the robust modal filter 30 requires.

Aircraft aeroelastic behavior is a function of the modal coordinates. By controlling modal coordinates, one may control the shape of the vehicle. The shape of the vehicle is intrinsically related to the aerodynamic performance of the vehicle. Thus control of the modal coordinates can lead to control of aeroservoelastic performance of the vehicle. The robust modal filter software 30 robustly computes the required modal coordinates for aeroservoelastic control through the computed modal matrices and on-line real time distributed sensor (preferably strain) measurements.

The data from software 20 are input to a robust modal filter software module 30, which manages the contribution of the thousands of sensors 5 in the system and converts the information through concentration and M-estimation into the modal coordinates of the system. Thus, the modal filter 30 performs a multiple degree of freedom modal coordinate transformation. In accordance with the present invention, the robust modal filter 30 performs online robust regression rather than a least-squares regression, to significantly reduce sensitivity to outlier data. Ordinary least squares can give misleading results if the error variation of each sensor is not normal; thus ordinary least squares is highly susceptible to asymmetric sensor noise and/or sensor failure. The present robust regression method (to be described) is designed to be not overly affected by violations of assumptions by the underlying data-generating process. A concentration algorithm is proposed as a basis for the robust modal filter derivation as they are applicable to large data sets. E. A. Fox, Q. F. Chen, and L. S. Heath. "A Faster Algorithm For Constructing Minimal Perfect Hash Functions", Proc. 15th Annual Int'l ACM SIGIR Conf. on Research and Development in Information Retrieval, pp 266-273 (1992). Typically robust regression methods for 1,000s of measurements are not computable in real time. The robust modal filter 30 solves this with a careful mix of M-estimation and concentration principles and introduces a new trim criterion.

The modal coordinates output from the robust modal filter 30 are input to a Function Approximator 60. Other inputs to the Function Approximator 60 may include distributed aerodynamic sensors and optionally fuel gauge information. With this information, a functional relationship between the modal coordinates and the aerodynamic sensors can be generated. The relationship is passed to a flight controller 50 which includes a diagnostics and performance analyzer module 70. The diagnostics and performance analyzer module 70 estimates performance optimization, stability and control measures needed to command the shape of the aircraft to an optimal shape while staying within constraint boundaries. These functional parameters are then sent to a command optimizer 80 which confirms the optimal flight system commands to implement the optimal shape. Finally, the optimal commands are assembled in a command shaping module 90, which gives the actual command setpoint to the active control system. All the foregoing components are described below in more detail.

Sensors 5

Figure 2:
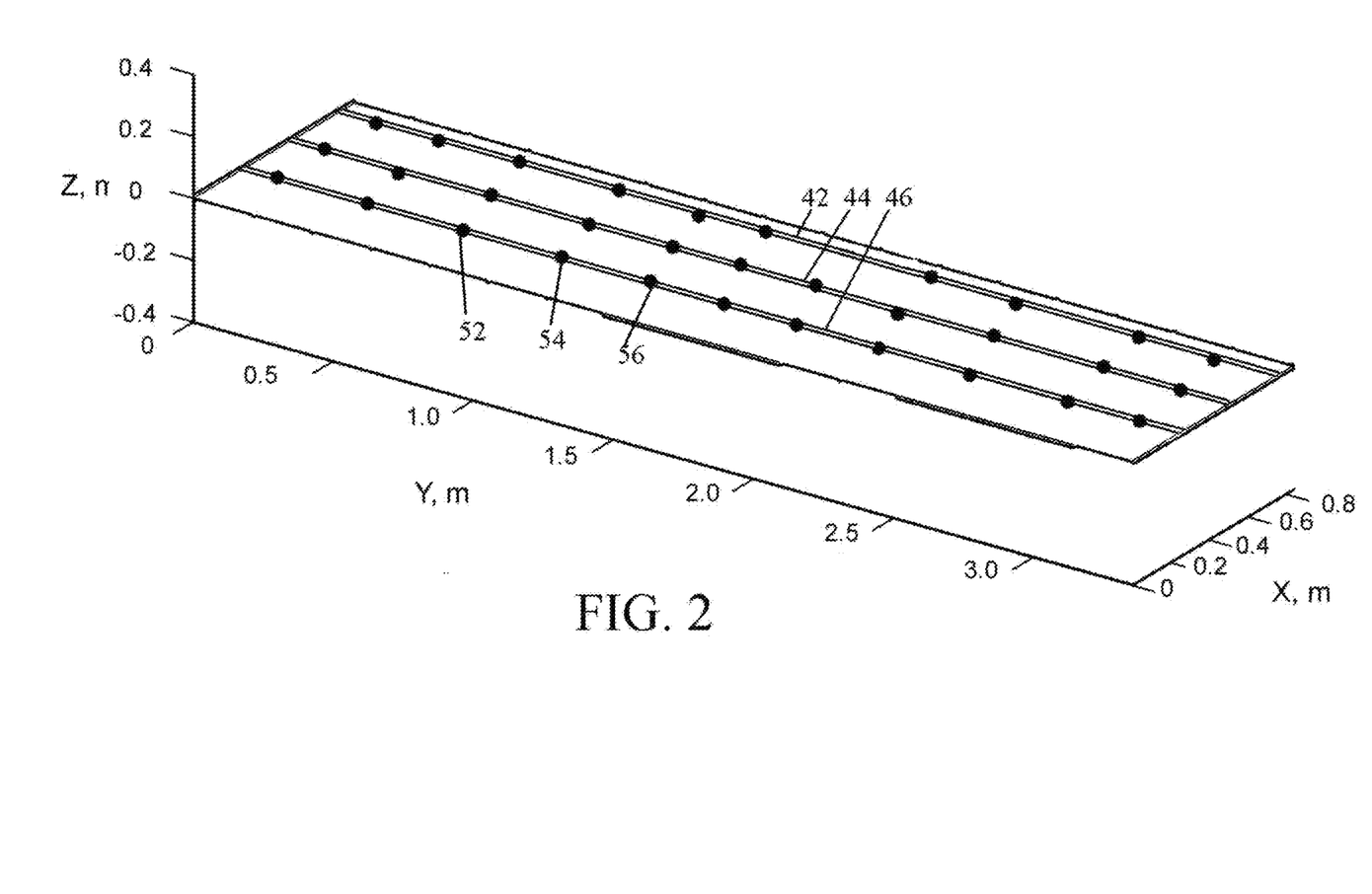
FIG. 2 illustrates the FOSS system on wing 2.

The present invention employs a fiber-optic sensing system (FOSS) 2 comprising a plurality of parallel optical fibers running along each wing and each having numerous Fiber Bragg gratings 5 ("FBGs") interposed along the length an optical fiber, spaced at approximately every ½".

FIG. 2 illustrates the FOSS system 2 on a wing including three parallel optical fibers 42, 44, 46 running along wing 2 and each having a plurality of FBGs 52, 54, 56 . . . interposed along the length. To capture sufficient bending information, the sensors 5 are placed span-wise along the entire wing. To capture torsional effects, a plurality of fibers 42, 44, 46 (e.g., three) are placed chord-wise. The spacing between each sensor 52, 54, 56 location along each fiber was set at ½-inch intervals.

Light from a tunable laser source (TLS) is split between reference and measurement arms of an interferometer. In the measurement path, the light is further split to interrogate each single-mode optical fiber and return the reflected light. The laser is swept so that back reflections from points at different distances along the fiber under test correspond to different beat frequencies. The reflection positions along the fiber can be distinguished by their different beat. The software 20 processes the strain measurements from sensors 5 to derive a highly accurate depiction of how each fiber is positioned, and smooths the data so that derivatives of the modal displacements can be taken to achieve modal velocities. The assembler software 20 calculates a modal matrix representing spatial or strain information at each sensor 5 using the finite element method. The assembler software 20 then reduces the modal matrix according to which sensors 5 are used. The distributed measurements from sensors 5 and reduced modal matrix (either shape or strain as per above) are then sent to the robust modal filter 30 for computation of the modal coordinates.

Robust Modal Filter 30

The design of modal filter 30 from an array of sensors 5 requires the output signals of each sensor 5 to be weighted based on their estimated variance. The measured strain is approximately a linear combination of the sensor 5 strain data matrix, and so the measured strain is asymmetrically distributed. Importantly, wing loading varies with aerodynamic condition, and so the underlying strain distribution is difficult to predict. Without a known symmetrical distribution, application of most computationally efficient robust outlier detection methods is challenging. This strain mode filter problem is herein solved using the derived concentrated modal estimator (CME) for robust modal filter 30.

The CME modal filter 30 operates by a recursive sequence of steps to provide modal coordinate estimates from data which is closest to the computed (in the algorithm step) statistical multivariate center of the data. The derivation of the robust modal filter is comprised of an M-step and concentration step. The M-steps occur within each concentration step. The CME modal filter 30 concentration step trims outliers, and then within this concentration step there are multiple M-estimation steps. As described below, during M-estimation the weights are computed based on the computed variance of the sensors 5. The weights used in M-estimation downweight or upweight a particular sensor's importance when estimating the modal displacements. Importantly, the M-step requires the concentration step (trimming of gross outliers based on trim criterion) or it will fall into a local minimum and become biased. Therefore the M-estimator and concentration estimator of CME modal filter 30 work synergistically. These substeps are described in more detail below and the M-step derivation is given first:

a. M-Step Derivation

The CME modal filter 30 utilizes M-estimates within each concentration step. M-estimators are well-known gradient descent algorithms. They are computationally efficient, affine equivariant, robust to masking effects. The strain at measurement locations may be expanded as a summation of an infinite number of orthogonal strain mode shapes (Eq. (0.33)).

$$s_k(x_c, y_c, z_c, t) = \sum_{i=1}^{\infty} q_i(t)\psi_i(x_c, y_c, z_c) \qquad (7.1)$$

To reduce model complexity, only a subset m of mode shapes which dominate the response are included in the strain modal matrix. It is assumed that the subset of modes captures the contributing dynamics and the sensors 5 are subject to random normal error. This introduces an error term into Eq. (0.33) which can be modeled as a normal distribution $\epsilon_k \in N(\mu_n, \sigma_n)$. At any discrete time $t=\tau$, the quasi-static approximate reading of any sensor 5 can be given as in Eq. (0.1), $$s_k(x_c, y_c, z_c, \tau) = \sum_{i=1}^{m} q_i(\tau)\psi_i(x_c, y_c, z_c) + \varepsilon_k \qquad (0.1)$$

where m is the number of mode shapes retained in the model. Consider the linear model for the $k^{th}$ sensor measurement to be described by Eq. (0.2), $$s_k(x_c, y_c, z_c, \tau) = \sum_{i=1}^{m} \hat{q}_i(\tau)\psi_i(x_c, y_c, z_c) + e_k = \Psi_k(x_c, y_c, z_c)q(\tau) + e_k \quad (0.2)$$

where $e_k$ is a finite residual (i.e. measurement error), $\Psi_k(x_c, y_c, z_c) \in \mathbb{R}^{1 \times k}$ is the $k^{th}$ row of the strain matrix. $\hat{q}(\tau) \in \mathbb{R}^{k \times 1}$ is a vector of estimated modal displacements. From the sensor 5, 6 readings, the objective is to estimate $\hat{q}(\tau)$. This can be solved as a maximum likelihood estimation (MLE) problem which is posed as minimization of an equally weighted summation of a function of the residuals (See Eq. (0.3)).

$$\sum_{k=1}^{s} \rho(e_k) = \sum_{k=1}^{s} \rho(s_k(x_c, y_c, z_c, \tau) - \Psi_k(x_c, y_c, z_c)\hat{q}(\tau)) \quad (0.3)$$

where S is the set of strain sensors and $\rho(x)$ is an objective function with special properties. A reasonable $\rho(x)$ must be symmetric, zero when evaluated at zero, increasing for increasing arguments and differentiable.

Define the influence function $\phi(x) = \rho'(x)$ as the differential of the objective function $\rho(x)$. The influence function characterizes the proportional impact of the residuals on the estimate. The impact of an OLS residual on the estimate is directly proportional to the size of the residual, which is why OLS is not robust. To find $\hat{q}(\tau)$ the summation given in (0.3) is differentiated by $\hat{q}(\tau)$ and is set equal to zero. By completing this, the following equality is achieved (See Eq. (0.4)).

$$\sum_{k=1}^{s} \varphi(s_k(x_c, y_c, z_c, \tau) - \Psi_k(x_c, y_c, z_c)\hat{q}(\tau))\Psi_k(x_c, y_c, z_c) = 0 \quad (0.4)$$

Let $w_k(e_k) = \phi(e_k)/e_k$ for any $\phi(e_k)$ then the weighted objective function can be rewritten as in Eq. (0.5), $$\sum_{k=1}^{s} w_k(e_k)(s_k(x_c, y_c, z_c, \tau) - \Psi_k(x_c, y_c, z_c)\hat{q}(\tau))\Psi_k(x_c, y_c, z_c) = 0 \quad (0.5)$$

which results in the weighted least squares problem. Equation (0.5) can be solved as a system of equations. Under normal conditions an efficient estimate of $\hat{q}(\tau)$ can be calculated. The weights $w_k(e_k)$ are affine equivariant and modeled as functions of the residuals $e_k$. The residuals are dependent upon the weights.

Therefore the method of iteratively reweighted least squares (IRLS) is used to solve the optimization problem. This proceeds by solving for an initial least squares estimate $\hat{q}(\tau)$ and computing the residuals and weights. Using the weighted observations a new feature estimate $\hat{q}(\tau)$ is computed and the residuals and weights are recalculated. The features or modal displacements $\hat{q}(\tau)$ of the hyperplane approximately satisfying for all sensors, Eq. (0.5) appears within a few iterations.

b. M-step Operation Within a Concentration Step

The solution of Eq. (0.5) must be computed within each concentration step, c for the proposed concentrated estimator. To improve the convergence to the unbiased solution of $\hat{q}(\tau)$ sensors 5 6 which are most outlying are completely removed. For the new group of sensors, M-estimation is used to find improved feature estimates. Selection of the influence function is critical to the M-estimator's performance. For its gross outlier rejection capability, Tukey's bisquare (also known as biweight) function is the preferred choice. The function is chosen to compute the weights with the residuals of the data. The bisquare weighting function $w = \phi(x)/x$ is defined for the $k^{th}$ sensor as in Eq. (0.6), $$w_k^{(b,c)}\left(\frac{e_k^{(b,c)}}{\sigma_k^{(b,c)}}\right) = \begin{cases} \left(1 - \left(\frac{e_k^{(b,c)}}{\sigma_k^{(b,c)}}\right)^2\right)^2 & \left|\frac{e_k^{(b,c)}}{\sigma_k^{(b,c)}}\right| < h_0 \\ 0 & \text{otherwise} \end{cases} \quad (0.6)$$

where $\sigma_k^{(b,c)}$ is the median absolute deviation (MAD), $h_0$ is a tuning constant, c is a concentration step, and b is an IRLS iteration count of the M-estimator. To achieve the maximum 95% asymptotic efficiency assuming residuals have a Gaussian distribution, a tuning constant of, for example, $h_0 = 4.685$ is required.

The MAD for the $k^{th}$ observation is calculated as in Eq. (0.7), $$\sigma_k^{(b,c)} = \text{MED}(|e_k^{(b,c)} - \text{MED}(e^{(b,c)})|)/0.6745 \quad (0.7)$$

where the constant scaling 0.6745 is required to achieve a 37% Gaussian efficient consistent estimator of the standard absolute deviation. While relatively low efficiency, the purpose of using MAD instead of using the true scale is to resist outliers. This it achieves remarkably well since the median is high breakdown. However, The MAD is developed for symmetric distributions and does not address distribution skewness. This may be of concern since the explanatory data is multivariate skewed. Improvements of the MAD approximation for asymmetric long-tailed distributions are available if necessary. Given the weights, $w_k^{(b,c)}$ the linear system of equations is solved for $\hat{q}^{(b,c)}(\tau)$ given sensors in subset $S_g^c$ as in Eq. (0.8).

$$\sum_{k=1}^{s_g^c} w_k^{(b,c)}\left(\frac{e_k^{(b,c)}}{\sigma_k^{(b,c)}}\right) \quad (0.8)$$

$$(s_k(x_c, y_c, z_c, \tau) - \Psi_k(x_c, y_c, z_c)\hat{q}^{(b,c)}(\tau))\Psi_k(x_c, y_c, z_c) = 0$$

The weighted least squares problem for the $c^{th}$ concentration step is solved in the same way as Eq. (0.5). Equations (0.6)-(0.8) are the primary feature estimator equations used within the concentration operator. They are iterated within any concentration step for a specified number of M-steps, $b_f$ resulting in $\hat{q}^{(b_f,c)}(\tau)$. The next section shows how this estimate is used to trim data through concentration before reapplying M-estimation.

c. Concentration Operation

The purpose of concentration is to iteratively remove poor observations and asymptotically approach the true statistical center of the data distribution. Utilizing sensors 5 nearest to this centroid are assumed to give the best feature estimates. A best estimate of this center is the multivariate location T and dispersion V of the data. A redescending M-estimator is a robust estimator of multivariate location and dispersion for theoretical asymmetric distributions.

Sensors furthest from this centroid are downweighted in Eq. (0.8). However, it is proposed to not just down-weight sensors, but to completely remove some gross outliers from consideration. The redescending M-estimator does in fact equate weights to 0 for gross outliers. The weighted sensor removal methodology to improve gross outlier rejection is developed here. Let the k sensor data vector be defined as in Eq. (0.9), $$x_k \triangleq [\Psi_k(x_C, y_C, z_C) s_k(x_C, y_C, z_C, \tau)] \quad (0.9)$$

Defining the data vector in this way ensures that outliers which depend on sensor readings shall not occur in the explanatory data. Only fixed outliers can occur in the explanatory data, which are to be addressed with a fixed trim criterion. From any sample sensor set $S_g^c \supseteq S$ a location vector (See Eq. (0.10))

$$T^{(b_f,c)} = \frac{1}{\sum w_k^{(b_f,c)}} \left( \sum_{k=1}^{s_g^c} w_k^{(b_f,c)} x_k \right) \quad (0.10)$$

and dispersion matrix [See Eq. (0.11)]

$$V^{(b_f,c)} = \sum_{k=1}^{s_g^c} w_k^{(b_f,c)} x_k^T x_k \quad (0.11)$$

are estimated in the $c^{th}$ concentration step. The weightings are the result of $b_f$ iterative M-steps over the subset of sensors $S_g^c$.

For the estimated location and variance, the squared Mahalanobis distance ($D^2$) (a descriptive statistic that provides a relative measure of a data point's residual distance from a common point.) is computed for every sensor data point k as in Eq. (0.12).

$$D^2(x_k) = (x_k - T^{(b_f,c)})(V^{(b_f,c)})^{-1}(x_k - T^{(b_f,c)})^T \quad (0.12)$$

This multivariate distance differs only from the Euclidean distance only in that it accounts for correlations between data points and is scale-invariant. If the population has a multivariate normal distribution, the $D^2$ is asymptotically approximated by a chi-square distribution. With this knowledge, statistical cutoff points from the inverse cumulative distribution can be determined. The initial distribution of $D^2$ may be computed from the fixed modal matrix and time varying set of strain data with Gaussian noise. The maximum of the computed $D^2$ may be used as an upper bound for removing gross outliers using iterative concentration. During each concentration step gross outliers are removed and the location and dispersion are re-estimated. The sample location and dispersion more closely resemble the population location and dispersion. Therefore the small outliers become more pronounced. As the $D^2(x_k)$ increases the sensor can be identified as an outlier and removed. Outliers missed by this trim procedure will more likely be down-weighted in the M-estimate [See Eq. (0.8)]. Finding the upper bound $D_{ub}^2$ is time consuming to implement requiring 1,000s of simulations since the strain is time varying. Since most of the data is described by the constant strain data matrix, an approximation can be used for the upper bound. It can be assumed that the distribution of $D^2(x_k)$, k=1 . . . S is equal to or greater than the distribution of $D^2(\Psi_k(x_c,y_c,z_c))$, k=1 . . . S if the sensor data has a Gaussian error distribution. With this assumption, the impact of an additional feature may be assumed to change the distribution of $D^2$ by the additional degree of freedom (DOF) impact in a chi-square distribution. Recall that $D^2$ is given in units of variance. This implies that the variance will increase with the additional DOF. Therefore it can be assumed that $D^2(\Psi_k(x_c,y_c,z_c)) + \theta(n_s) \geq D^2(x_k)$, k=1 . . . S. Assuming the adjustment of $\theta(n_s)$ is due to the noise of the strain data the scalar upper bound is defined as in Eq. (0.13):

$$D_{ub}^2 \triangleq P_c \max_{k \in S} D^2(\Psi_k(x_C, y_C, z_C)) \quad (0.13)$$

where $P_c$ is a tuning constant chosen to be slightly greater than 1. The tuning constant accounts for $\theta(n_s)$. By removing a portion $k \in S$ sensors with $D^2 < D_{ub}^2$ a new candidate group of sensors $S_g^{c+1}$ is found for the next concentration step, and consecutive M-steps. Simulation studies verify this approximation of the upper bound, $D_{ub}^2$ to be good for the strain mode matrix and strain data.

d. Robust Starts and Operations

Robustness for multi-stage estimators tends to come from good starts (initial feature estimates). An initial feature estimate from a high breakdown estimator is used to start the M-estimator for MM-estimates. The median ball algorithm proposed by Olive (2004) uses feature estimates from sensors closest to the median as a robust start, and is a good choice inasmuch as it works reasonably well for nominally skewed distributions. The first estimate of the system when $\tau$ is 0, (i.e. when the sensor system is first operational), is calculated with a non-robust least squares estimate. Since the first estimate is assumed to come from a working sensor system it is a robust estimate. The initial robust feature estimate $\hat{q}^{(0,0)}(0)$ is found by solving the least squares problem presented in Eq. (0.14), $$\sum_{k=1}^{s_g^0} \left( s_k(x_c, y_c, z_c, \tau) - \Psi_k(x_c, y_c, z_c) \hat{q}^{(0,0)}(0) \right) \Psi_k(x_c, y_c, z_c) = 0 \quad (0.14)$$

where $S_g^0$ is the set all of the available working sensors.

During operation, a robust start is paramount. A significant advantage of a time based sensor system is that previous close estimates are available. The most robust start will therefore be the estimate from the previous time step. This is because the strain change is assumed to be small between discrete time steps. Thus, the robust starts between discrete time steps are implemented as in Eq. (0.15), $$\hat{q}^{(0,0)}(\tau) = \hat{q}^{(b_f,c_f)}(\tau-1) \quad (0.15)$$

where $b_f$ is the total number of M-steps chosen and $c_f$ is the total number of concentration steps.

The importance of starts carries over into the concentration steps themselves. In order to be high breakdown, each concentration step requires a robust start. Since the initial start $\hat{q}^{(0,0)}(0)$ is robust the final estimates at the end of each of the concentration steps:

$\hat{q}^{(b_f,1)}(\tau), \hat{q}^{(b_f,2)}(\tau), \ldots \hat{q}^{(b_f,c_f-1)}(\tau)$ are robust. This mean that the estimates of corresponding concentration steps are robust starts for respective next concentration steps:

$\hat{q}^{(0,2)}(\tau), \hat{q}^{(0,3)}(\tau), \ldots \hat{q}^{(0,c_f)}(\tau)$. Therefore the following inheritance rule [See Eq. (0.16)] is used to generate robust starts between concentration steps:

$$\hat{q}^{(0,c+1)}(\tau) = \hat{q}^{(b_f,c)}(\tau) \quad (0.16)$$

The full steps of the CME modal filter 30 for any discrete time step are summarized in Algorithm 1 assuming that an initial OLS feature estimate has already been computed with Eq. (0.14) at time 0.

$$\{s_k(x_c, y_c, z_c, \tau), \hat{q}^{(b_f,c_f)}(\tau-1)\} \rightarrow \hat{q}^{(b_f,c_f)} \quad \text{Algorithm 1}$$

1) If c==0, compute $\hat{q}^{(0,0)}(\tau)$ with Eq. (0.15). Else compute $\hat{q}^{(0,c)}(\tau)$ with Eq. (0.16).
2) For b=0: $b_f$, Iteratively compute weights, $w_k^{(b_f,c)}$ with Eqs. (0.6)-(0.8) with $\hat{q}^{(0,c)}$
3) Compute location T (See Eq. (0.10)) and dispersion V (See Eq. (0.11)) with computed $w_k^{(b_f,c)}$
4) Compute $D^2(x_k)$, k=1 ... S, using Eq. (0.12) with computed T and S
5) Generate a new sensor set $S_g^{c+1}$ by trimming sensors below cutoff $D_{ub}^2$ described by Eq. (0.13).
6) If c<$c_f$, Go to Step 1. Else output $\hat{q}^{(b_f,c_f)}(\tau)$.

For each time step, the M-step iteration count $b_f$ may be initialized to be large, so that a robust redescending M-estimate initializes the CME modal filter 30. This improves the algorithm's stability during the concentration steps. Afterwards, single M-steps where $b_f$ is equal to 1, may be utilized. This has the effect of improving computational efficiency.

The CME modal filter 30 given by Algorithm 1 is robust estimator with more than 0.5 breakdown point given the use of robust starts which are estimates from previous time steps. By assuming that the initial estimate at time 0 occurs when the sensor system is operating normally, the OLS estimate at time 0 is robust. This robust estimate is used as a robust start to the next time step; the corresponding robust estimate is used for the start in the next time step and so on. Therefore robustness is guaranteed between time steps. Robustness is also guaranteed between concentration steps. Therefore, iterative application of the robustness inheritance concept guarantees robustness through all concentration operations.

Function Generator 60

The CME modal filter 30 outputs the modal coordinate estimates as an input to the Function Generator 60. The aircraft must also provide the network with local aerodynamic information and possibly fuel gauge information. The Function Generator 60 takes the modal coordinates from CME modal filter 30 and aerodynamic information and iteratively updates a functional relationship between the two.

The function generator 60 approximates an unknown function of the modal coordinates F(modal coordinates) based on aerodynamic data, such that the aerodynamic state=F(modal coordinates). Of course, in order to determine what F is, local aerodynamic data must be provided and so some measurement of aerodynamic state is necessary. Consequently, aerodynamic state sensor(s) such as hot film strips or leading edge sensors for monitoring pressures over the wing surface (for optimal drag configuration), fuel rate sensors (for fuel efficiency), or any other suitable sensor(s) for measuring aerodynamic state are provided. For example, given fuel rate sensors it is possible to form the functional relationship fuel rate=F(modal coordinates). Once the function generator 60 approximates the function F, it becomes possible to know where to command the modal coordinates to in order to achieve the optimal aerodynamic state (e.g., optimal drag efficient shape).

The function generator 60 is passed to the flight controller 50 for analysis. From the analysis, a minimum drag aircraft control surface configuration for fuel savings can be attained, or flutter suppression, etc. In effect, aircraft inflight shape optimization becomes possible given the structural states measured. The function approximator 60 may comprise a neural network that employs on-line learning and computes functional relationship changes in the plant 10. The Flight Controller 50 computes the required control surface deflections for an optimal drag configuration. An example of a aeroelastic control neural network is presented in U.S. Pat. No. 7,617,166 to Haudrich et al.

Flight Controller 50

The function generator 60 is input to a Flight Controller 50 in the vehicle, which may be an existing flight controller programmed with the requisite control modules 70, 80, 90 of the present invention. Specifically, Flight Controller 50 includes a diagnostics and performance analyzer module 70 which analyzes the function output from function generator 60 and estimates the optimal modal coordinates to correct to, as necessary to achieve performance optimization, stability & control measures needed to command the shape of the aircraft to an optimal shape. The optimal modal coordinates from performance analyzer module 70 are sent to an Optimizer 80, which is a function approximator similar to 60 and can be interrogated to find the optimal control surface settings. Optimizer 80 may likewise be a neural network or a less-complex function solver such as a genetic algorithm. A genetic algorithm is a known method for finding globally optimal solutions for a given function. See, e.g., Mitchell, "An Introduction to Genetic Algorithms", Cambridge, Mass., MIT Press (1996). Finally, the optimal control surface settings from Optimizer 80 are sent to Command Shaping Module 90 which computes the optimal flight system commands to implement the optimal shape and compiles the command set for input to the existing active control system.

The following examples illustrate the above-described system in more detail.

Example 1

The above-described system has been verified with a simple FEM model of a wing developed using MATLAB/Simulink™. The wing model allowed the user to input aspects such as wing span and chord, as well as number and location of control surfaces. The finite element model was coupled with an unsteady aerodynamics model and gust model captured by Rational Function Approximations (RFAs) of the generalized forces found through frequency based linear aerodynamic methods. Fighter aircraft type actuators were utilized for dynamic control surface simulation. State space models were formed and a simulated modal filtering system was designed. The state space models were also utilized for control design. The system was implemented with an array of fiber optics with FBG sensors. The wing model was structurally simple.

Example 2

Figure 3:
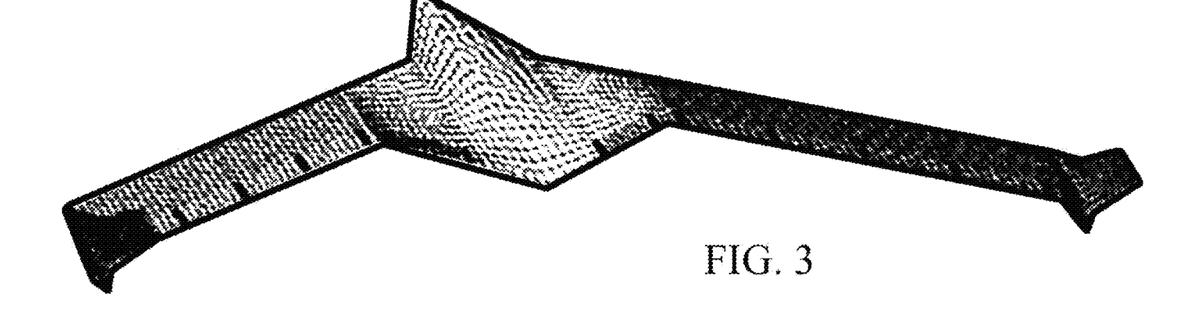
FIG. 3 illustrates the complex X-56A aircraft model of Example 2.
Figure 4:
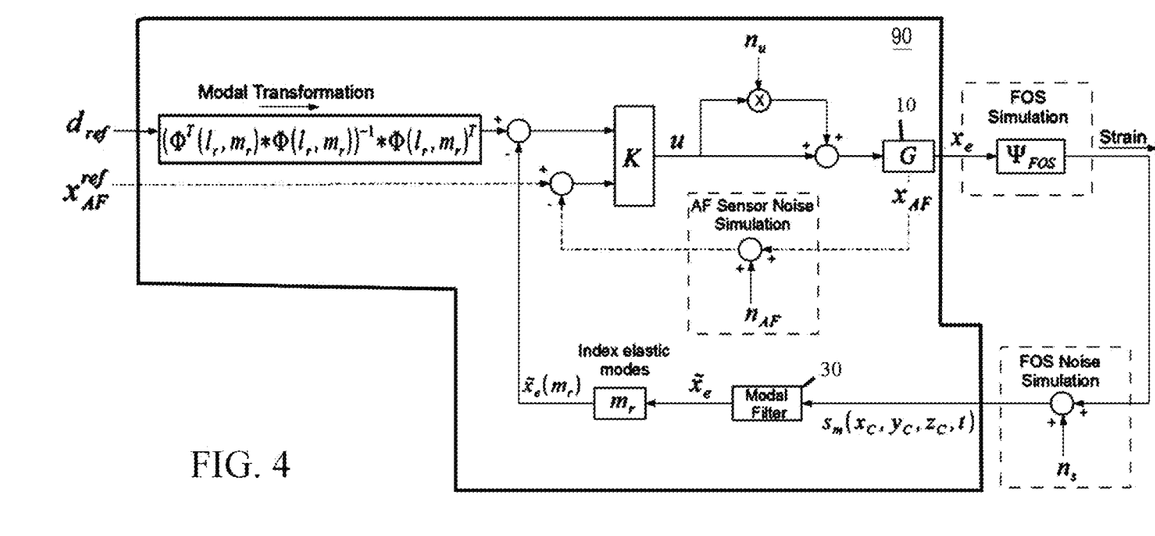
FIG. 4 is a schematic of the command shaping module 90 of FIG. 1 applied configured for design for the X-56A model of FIG. 3.
Figure 5:
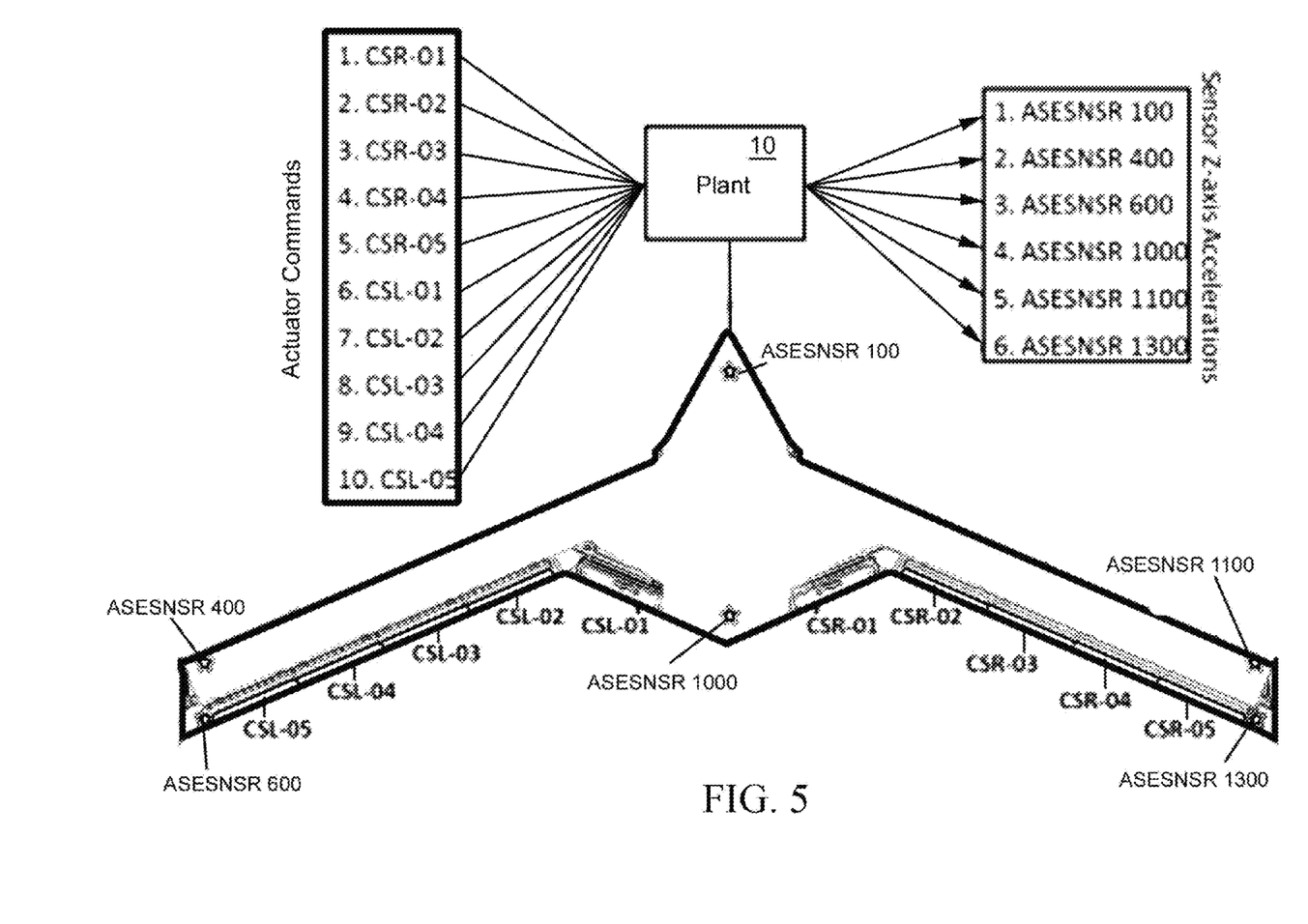
FIG. 5 is a diagram of the accelerometer sensor 6 and FBG sensor 5 control surface locations used for the X-56A state-space model of FIG. 4.

The above-described system has been verified with a complex X-56A aircraft model as shown in FIG. 3. The design of the Command Shaping Module 90 (from FIG. 1) is shown in FIG. 4. This architecture assumes a virtual deformation control architecture with modal reference tracking. Since deformation is directly related to modal displacements, the significant modal displacements are commanded directly, thereby leading to deformation changes in the vehicle. This is what is referred to by virtual deformation control architecture. Note that the FOS simulation and FOS Noice Simulations at right would be replaced by the FOSS Sensing System 2 of FIG. 1 in a real-aircraft implementation.

Identification of significant modes in an aircraft structure is similar to that for a wing model. V-g and V-f plots or equivalent may be used to determine interacting modal coordinates, and modal coordinates must be selected for feedback which contribute to flutter, modal vibration and are within the actuator bandwidth. Selection of these modes can be an iterative process. Once feedback modes have been decided upon, the state space matrices are updated. The matrix equation of motion of the aeroelastic system in discrete coordinates is given as in Eq. (0.17).

$$[M_{hh}]\{\ddot{q}\}+[C_{hh}]\{\dot{q}\}+[K_{hh}]\{q\}+[M_{hc}]\{\ddot{\delta}\}= q_\infty[Q_{hh}(ik)]\{q\}+q_\infty[Q_{hc}(ik)]\{\delta\} \quad (0.17)$$

Analogous to Euler's first law, F=ma (or in this case ma=F), the left side of the aeroelastic system equation represents the structure's mass properties and applied motion while the right side represents the aerodynamics forces. The aero module includes several components such as aero paneling, aero modes and gust modes, as well as GAF calculation and RFA design. Points between the FE model and aero model are selected that accurately represent the force transferal from the aerodynamic control points to the structural grid points. This allows calculation of the GAFs from modal deformation at structural grid points. It is necessary to convert the frequency-domain GAF to the Laplace domain. However, the Laplace-domain unsteady aerodynamics must be in a rational function form to be incorporated into the time-domain state-space equations of the aeroelastic system. Therefore, the unsteady aerodynamic forces are approximated through the following RFA as in Eq. (0.18).

$$\left[\tilde{Q}(ik_i)\right] \approx [A_o] + [A_1](ik_i) + [A_2](ik_i)^2 + [D]\left[ik_i[I] - \frac{V}{L}[R]\right]^{-1}[E](ik_i) \quad (0.18)$$

From principles of analytic continuation, the unsteady aero modeled in terms of reduced frequencies can be expanded into the entire Laplace domain through the following substitution given in Eq. (0.19), $$\frac{L}{V}s = g + ik \quad (0.19)$$

where s is the Laplace Variable and g is the non-dimensional damping. Aero lags are used to model the delayed force effects of the unsteady aerodynamics. The aero lags are modeled as zeros along the negative real axis of the Laplace domain since the aero force translation to the structure is not real time. By setting g=0, for the non-dimensional damping, the aerodynamic forces are now expressed in the Laplace domain as in Eq. (0.20).

$$\left[\tilde{Q}(s)\right] = \begin{bmatrix} Q_{hh} \\ Q_{hc} \end{bmatrix} = [A_o] + \frac{L}{V}[A_1]s + \frac{L^2}{V^2}[A_2]s^2 + [D]\left[s[I] - \frac{V}{L}[R]\right]^{-1}[E]s \quad (0.20)$$

Roger's method was chosen to compute the RFA. Constraints are applied at specific reduced frequencies (such as at zero) and aerodynamic derivatives may be matched using the ZAERO™ software system by Zona Technologies, Inc., a software tool for advanced aeroelastic design and analysis (by running open-loop ASE analysis in frequency domain first, e.g., normal flutter analysis, and then comparing with open-loop analysis in the time domain using state-space models to ensure the RFA is accurate). The state vector is shown in Eq. (0.21), $$x(t) \triangleq \{x_{AF}(t), x_g(t), \dot{x}_g(t), x_{lag}(t), x_{act}(t)\}^T \quad (0.21)$$

where $x_{AF}(t) \in \mathbb{R}^{AS \times 1}$ is a vector of airframe states, $x_e(t) \in \mathbb{R}^{m \times 1}$ is a vector of modal displacements, $\dot{x}_s(t) \in \mathbb{R}^{m \times 1}$ is a vector of modal velocities, $x_{lag}(t) \in \mathbb{R}^{f \times 1}$ is a vector of aerodynamic lag states and $x_{act}(t) \in \mathbb{R}^{s \times 1}$ is formed from a vector of actuator accelerations, velocities, and displacements.

Trim conditions were applied to the nonlinear equations of motion to develop the state space models. The trim analysis ensures gravity is included into the model to provide more accurate flight responses for rigid body motion. In addition, a 1G gravitational force was applied and the only free variable was the angle of attack. These conditions lead to a trim angle of attack and a trimmed elastic solution. Therefore all the state space models' states are considered to be perturbations about this point.

The state space models must also model actuator dynamics. A third order transfer function of the actuators is formulated for each control surface to incorporate the actuator dynamics into the system. The actuator transfer function is represented in Eq. (0.22).

$$\frac{\delta_1(s)}{u_{ac_1}(s)} = \frac{a_{i3}}{s^3 + a_{i1}s^2 + a_{i2}s + a_{i3}} \quad (0.22)$$

The LTI transformation resolves the transfer function into actuator state space matrices of the as in Eq. (0.23).

$$\{\dot{x}_{act}\} = \begin{bmatrix} 0 & 1 & 0 \\ 0 & 0 & 1 \\ -a_{i3} & -a_{i2} & -a_{i1} \end{bmatrix} \{x_{act}\} + \begin{Bmatrix} 0 \\ 0 \\ a_{i3} \end{Bmatrix} u_{ac_i} \quad (0.23)$$

These models are appended to the state space models for all ten control surfaces, increasing the state space order by the order of the actuator transfer function multiplied by ten.

Sensors 5 which measure strain were also defined from modal matrix computations in NASTRAN™ (a finite element analysis (FEA) program originally developed for NASA in the late 1960s). The shape modal matrices were converted to strain modal matrices. The known simulation modal coordinates are used to back out strain measurements assuming superposition for small strain. This was done in lieu of using actual fiber optic sensor strain measurements, which would replace the above methodology.

The modification of the state space matrices for modal coordinate feedback is very similar to how the wing model state space matrices are modified. Consider the relationship of the strain-based modal filter to the modal displacement state vector $x_s(t)$ as in Eq. (0.24), $$x_s(t) = q(t) = (\Psi^T\Psi)^{-1}\Psi^T s_m(x_c, y_c, z_c, t) + \epsilon \quad (0.24)$$

where $\Psi = \{S_A \phi_i(x_c, y_c, z_c), i=1 \ldots N\}$ is a N×N strain matrix with N strain modes, $s_m(x_c, y_c, z_c) \in \mathbb{R}^{N \times 1}$ is the measured strain and ε is a normal error. This represents the modal filter in its pseudo-inverse form. Since the modal filter gives a partial state estimate of the full state vector, x(t) as defined in Eq. (0.21) the form of the output matrix is simply identity for measured modes. The sensor output matrix, C, is a matrix of row vectors relating the sensory information to the state vector, x(t). The output matrix is adjusted for rigid body state feedback concurrent with modal deformation state feedback. It is assumed that m modes are retained for measurement. The output matrix is formed assuming all modal displacements, $x_s$, and airframe states, $x_{AF}$, are measured, as shown in Eq. (0.25).

$$C \triangleq \begin{bmatrix} I_{AS \times AS} & 0_{AS \times m} & 0_{AS \times m} & 0_{AS \times f} & 0_{AS \times z} \\ 0_{m \times AS} & I_{m \times m} & 0_{m \times m} & 0_{m \times f} & 0_{m \times z} \end{bmatrix} \quad (0.25)$$

As with the wing model, there is no requirement to measure all flexible states (or rigid states) to adequately sense the vehicle state. Higher frequency modes generally do not significantly contribute strongly to the deformation and may be ignored to reduce the size of the C matrix.

After selecting and modeling modal coordinates, the state space matrices can be reduced in order and used to design the control laws. Similar to the wing model (Example 1), control design can proceed with any desired control methodology. For the wing model, the µ-Optimal design methodology was chosen. See, S. Skogestad and I. Postlethwaite, *Multivariable Feedback Control Analysis and Design*, West Sussex, England: John Wiley & Sons, Inc, 2005. Once the controller has been designed which meets requirements, the modal coordinates are also fixed. They can be used in the modal filter design.

The modal filter 30 for the X-56A is in units of strain measured directly from the FOSS sensors 5. To utilize a strain mode matrix for modal filter 30, the axial strain modes must be computed. The close proximity of the sensors (of approximately one-half-inch) along the SFOS gives a unique opportunity to calculate axial strain modes directly from the deformation at the sensor locations. An approximation of the strain mode matrix was made using the computed deformations for each mode shape at the sensor 5 locations. This relies upon a simple strain to displacement relationship which is a derivative. This can also be done by fitting a shape polynomial to the surface and taking a derivative at the desired points.

The transformed mode shapes defined at sensor locations are collected to form the modal matrix. These mode shapes are pure elastic and thus are used to form a proper modal reference transformation. The modal reference command is shown in Eq. (0.26):

$$q_{ref}(t) = \Phi^{\dagger}(l_r, m_r) d_{ref}(x_c, y_c, z_c, t) \quad (0.26)$$

where $d_{ref}(x_c, y_c, z_c, t)$ is a vector of deformations from the un-deformed aircraft corresponding to the index vector, $l_r$, in the pure elastic deformation modal matrix, O.

Recall that each row of the modal matrix corresponds to a physical location on the aircraft, $(x_c, y_c, z_c)$. The index of modes, $m_r$, corresponds to the index of modes within the modal matrix, which the controller is designed to track. The selection of $l_r$ is a research topic within itself. However, here it is recommended to select points with high deformation in the commanded mode shapes. A better technique would also select points which minimized residual mode amplitudes. This completes the modal filter 30 design methodology. The following sections put the presented modal filter design methodology into practice on the X-56A vehicle.

Once strain estimator 20 has captured the modal displacements of sensors 5, the Modal Filter 30 computes the modal matrix or transformation matrix, which is expressed as a sum of modal vectors.

The X56A is intentionally designed to encounter three flutter instabilities within its operating flight envelope: body freedom flutter (BFF), symmetric wing bending torsion flutter (SWBT), and antisymmetric wing bending torsion flutter (AWBT). BFF is a phenomenon where the rigid body mode of pitch and plunge couples with the elastic mode of first wing bending. The other two modes are traditional elastic flutter modes.

The BFF mode is demonstrated by the interaction of the scaled states, rigid body heave state, $\delta z_{cm}$, and modal displacement δSWB1. The flutter characteristics of the BFF mode are divergent oscillations of contributing modes at the same frequency, out of phase.

The SWBT mode also illustrates the unfavorable coupling of modal displacements: δSW1B and δSW1T. The nature of the coupling is difficult to discern because it appears random in nature. This means that there is an interaction with another mode, likely the BFF mode.

The AWBT mode shows an in-phase interaction of modal displacements: δAW1B and δAW1T. The scaled modal amplitudes are small but clearly grow in time, verifying that this flutter mode also exists at the design flight condition. Without control, the aircraft will experience strong flutter instability and will require AFS at this speed.

The flutter modes indicate that four flexible modal displacements should be used for control feedback, including δSW1B, δSW1T, δAW1B and δAW1T. However, the frequencies of the anti-symmetric modes are prohibitively high and close to the actuator bandwidth. Therefore only the symmetric $1^{st}$ bending and $1^{st}$ torsional modal displacements are selected for feedback. The requirements of the vehicle controller are now overviewed, and a µ-optimal controller is designed, which can track both rigid body states and the first two modal displacements.

Since flutter is a potentially destructive phenomenon, the modal controller must be robust to uncertainty. To reduce these uncertainties, the following uncertainty requirements were defined: 10 percent multiplicative uncertainty on the inputs and outputs, and 10 percent additive uncertainty on the scaled plant. In addition, the controller must be robust to a 3-percent speed variation. The controller must also achieve robust performance despite the aforementioned uncertainty conditions. The uncertain plant 10 and required control system 50 may be tested using the construct summarized in FIG. 6. This represents the requirements which the controller 50 must meet, and not necessarily how it is designed. Note that for other aircraft, these requirements may change.

The robust stability condition which must be met for the µ-optimal controller is given as in Eq. (0.27).

$$RS \Leftrightarrow \mu(M_\Delta(i\omega)) < 1, \forall \omega \quad (0.27)$$

The µ is calculated over the frequency range with the relation shown in Eq. (0.28), $$\mu(M_\Delta(i\omega)) = \frac{1}{\min\{k_m \mid \det(I - k_m M_\Delta(i\omega)\Delta) = 0 \text{ for structured } \Delta, \overline{\sigma}(\Delta) \leq 1\}} \quad (0.28)$$

where $k_m$ is the stability margin, $\overline{\sigma}$ is the maximum singular value, and Δ is the structured uncertainty. The transfer function matrix from the input of the uncertainty blocks to the outputs of them as shown in Figure Error! Reference source not found. is presented as in Eq. (0.29), $$M_\Delta = \begin{bmatrix} -W_I T_I & -W_I KS_O & -W_I KS_O \\ W_A S_I & -W_A KS_O & -W_A KS_O \\ W_O GS_I & W_O S_O & -W_O T_O \end{bmatrix}, G \varepsilon G_V \quad (0.29)$$

where $W_I$ is a matrix of proper input weights, $W_A$ is a matrix of proper additive weights, $W_O$ is a matrix of proper output weights, and K is the controller. From this matrix, the salient sensitivity and complementary sensitivities from the $M_\Delta$ structure are identified which correspond to the requirements. The magnitude of the singular values predict the performance of the control system. These closed loop transfer functions are defined as in Eq. (0.30), $$T_I = KG(I+KG)^{-1}$$

$$KS_O = K(I+GK)^{-1}$$

$$S_O = (I+GK)^{-1}$$

$$S_I = (I+KG)^{-1}$$

$$T_O = GK(I+GK)^{-1} \quad (0.30)$$

where $T_I$ is the input complementary sensitivity, $S_O$ is the output sensitivity, $S_I$ is the input sensitivity, and $T_O$ is the output complementary sensitivity.

Figure 7:
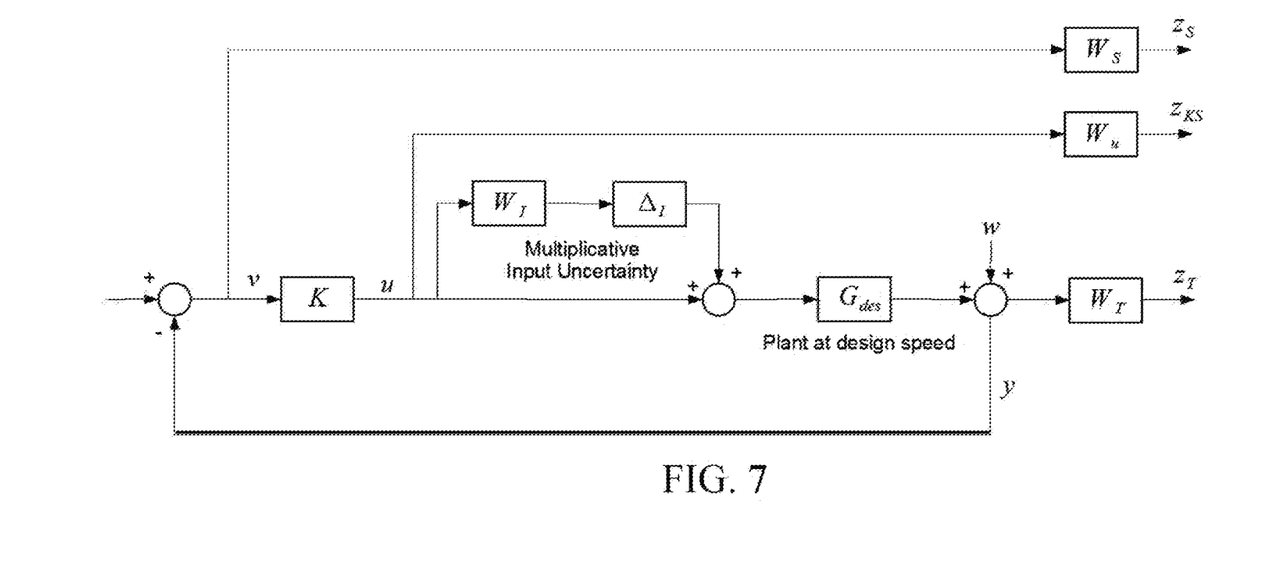
FIG. 7 is a schematic of the plant model used for the controller design of FIG. 1 to improve rejection of control input uncertainty. This construct may be used to test the flight controller 50 of FIG. 1.

To improve rejection of control input uncertainty, the controller 50 was designed around the plant construct shown in FIG. 7.

The design plant, $G_{des}$, at the design speed, $V_{des}$, was of order 130. To improve controller synthesis $G_{des}$ was scaled by the full range of actuator movement and expected sensor output changes. The translational states, $\delta x_{cm}$, $\delta y_{cm}$, and $\delta z_{cm}$, and the velocity state were removed from the model. With the resulting 126th-order model, balanced reduction was performed to bring the model order to 90 states. The selected states to be tracked were: SW1B and SW1T modal displacements, pitch angle, $\theta$, and bank angle, $\phi$. The angle of attack $\alpha$, angle of sideslip $\beta$, and yaw angle, $\psi$ were also sensed but were chosen to be suppressed.

Traditional proper weights from a mixed $H_\infty$ synthesis were utilized along with multiplicative uncertainty at the plant inputs. The input uncertainty weight, $W_I$, was adjusted to achieve maximum amplitude near the actuator break frequency. Sensitivity weight, $W_S$, was adjusted for integral tracking on tracking states and for suppression on suppression states.

It was found that the break frequencies of the modal displacement performance weights had to be increased 10 rad/s relative to the airframe state weight break frequencies of 1 rad/s. The break frequency of the control weight, $W_u$, was adjusted to 5 rad/s for reduced control surface movement. The break frequency of the complementary sensitivity weight, $W_T$, was set to 30 rad/s to improve high frequency noise rejection. The uncertainty transfer function, $N_\Delta$, was calculated to be as shown in Eq. (0.31):

$$N_\Delta = \begin{bmatrix} W_I T_I & -W_I KS_O \\ -W_S GS_I & -W_S S_O \\ -W_u T_I & -W_u KS_O \\ W_T GS_I & -W_T T_O \end{bmatrix} \quad (0.31)$$

Figure 6:
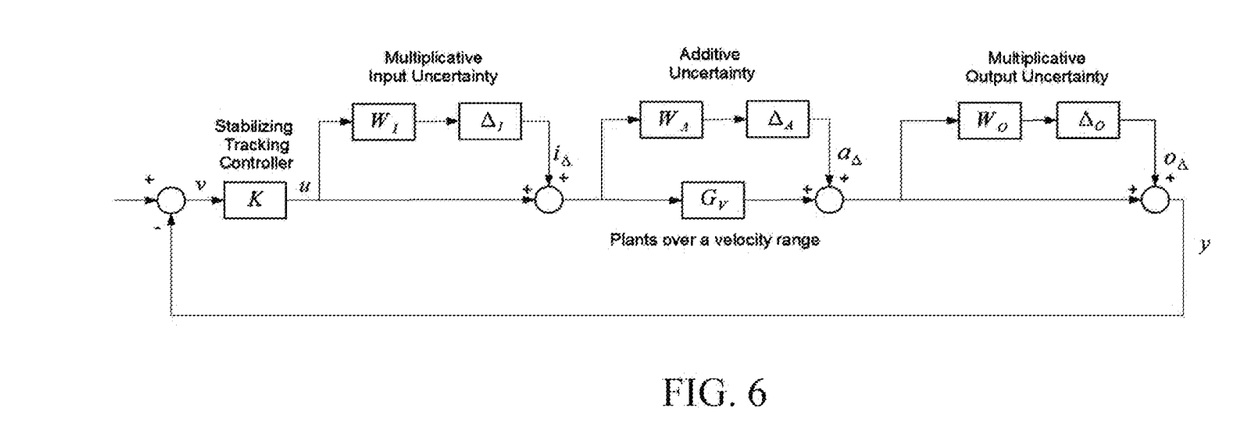
FIG. 6 is a schematic diagram of the uncertain plant and the required controller for the X-56A model. This construct may be used to test the flight controller 50 of FIG. 1.

Thus, by reducing the $H_\infty$ norm of $N_\Delta$, the specified uncertainties in FIG. 6 can be rejected.

For this control design architecture, the μ-optimal controller was computed using MATLAB's Robust Control Tool Box. To find the controller, a DK-iteration was performed as per S. Skogestad and I. Postlethwaite, *Multivariable Feedback Control Analysis and Design*, West Sussex, England: John Wiley & Sons, Inc. (2005), which solves the iterative optimization problem shown in Eq. (0.32).

$$\min_K \left( \min_{D_\omega} \| D_\omega N_\Delta(K) D_\omega^{-1} \|_\infty \right) \quad (0.32)$$

The DK-iteration resulted in a 162th-order controller after some trial and error with the weights in FIG. 7. The controller was then internally balanced and truncated to 44 states without a substantial loss of robustness or performance. This resulted in an $H_\infty$ norm of 3.29.

A concentrated modal estimator (CME) was then developed to form the basis for CME Modal Filter 30. The CME is primarily a concentration algorithm with re-descending M-estimates used in place of OLS within the concentration steps. The CME utilizes a fixed trim criterion and a more robust start to address asymmetry of the strain mode matrix data. For the X-56A sensor system fourteen modal displacement features are included in the strain mode matrix $\Psi$ corresponding to 1,530 sensor entries. Therefore, the problem is computationally burdensome and also multivariate. The strain at measurement locations may be expanded as a summation of an infinite number of orthogonal strain mode shapes (See Eq. (0.33)).

$$s_k(x_C, y_C, z_C, t) = \sum_{i=1}^{\infty} q_i(t) \psi_i(x_C, y_C, z_C) \quad (0.33)$$

To reduce model complexity, only a subset m of mode shapes which dominate the response are included in the strain modal matrix. It is assumed that the subset of modes captures the contributing dynamics and the sensors are subject to random normal error. This introduces an error term into Eq. (0.33) which can be modeled as a normal distribution $\epsilon_k \in N(\mu_n, \sigma_n)$. At any discrete time $t=\tau$, the quasi-static approximate reading of any sensor can be given as in Eq. (0.1), $$s_k(x_C, y_C, z_C, \tau) = \sum_{i=1}^{m} q_i(\tau) \psi_i(x_C, y_C, z_C) + \varepsilon_k \quad (0.34)$$

where m is the number of mode shapes retained in the model. Consider the linear model for the $k^{th}$ sensor measurement to be described by Eq. (0.2), $$s_k(x_C, y_C, z_C, \tau) = \qquad (0.35)$$

$$\sum_{i=1}^{m} \hat{q}_i(\tau)\psi_i(x_C, y_C, z_C) + e_k = \Psi_k(x_C, y_C, z_C)\hat{q}(\tau) + e_k$$

where $e_k$ is a finite residual (i.e. measurement error), $\Psi_k(x_c, y_c, z_c) \in \mathbb{R}^{1 \times k}$ is the $k^{th}$ row of the strain matrix. $\hat{q}(\tau) \in \mathbb{R}^{k \times 1}$ is a vector of estimated modal displacements. From the sensors readings, the objective is to estimate $\hat{q}(\tau)$. This can be solved as a maximum likelihood estimation (MLE) problem (See Huber [195]) which is posed as minimization of an equally weighted summation of a function of the residuals (See Eq. (0.3)), $$\sum_{k=1}^{S} \rho(e_k) = \sum_{k=1}^{S} \rho(s_k(x_C, y_C, z_C, \tau) - \Psi_k(x_C, y_C, z_C)\hat{q}(\tau)) \qquad (0.36)$$

where S is the set of strain sensors and $\rho(x)$ is an objective function with special properties. A reasonable $\rho(x)$ must be symmetric, zero when evaluated at zero, increasing for increasing arguments and differentiable.

Define the influence function $\phi(x)=\rho'(x)$ as the differential of the objective function $\rho(x)$. The influence function characterizes the proportional impact of the residuals on the estimate. To find $\hat{q}(\tau)$ the summation given in (0.3) is differentiated bye $\hat{q}(\tau)$ and is set equal to zero. By completing this, the following equality is achieved (See Eq. (0.4)).

$$\sum_{k=1}^{S} \varphi(s_k(x_C, y_C, z_C, \tau) - \Psi_k(x_C, y_C, z_C)\hat{q}(\tau))\Psi_k(x_C, y_C, z_C) = 0 \qquad (0.37)$$

Let $w_k(e_k)=\phi(e_k)/e_k$ for any $\phi(e_k)$ then the weighted objective function can be rewritten as in Eq. (0.5), $$\sum_{k=1}^{S} w_k(e_k)(s_k(x_C, y_C, z_C, \tau) - \qquad (0.38)$$

$$\Psi_k(x_C, y_C, z_C)\hat{q}(\tau))\Psi_k(x_C, y_C, z_C) = 0$$

which results in a weighted least squares problem. Equation (0.5) can be solved as a system of equations. Under normal conditions an efficient estimate of $\hat{q}(\tau)$ can be calculated. The weights $w_k(e_k)$ are affine equivariant and modeled as functions of the residuals $e_k$. The residuals are dependent upon the weights. Solve for an initial least squares estimate $\hat{q}(\tau)$ and compute the residuals and weights. Using the weighted observations a new feature estimate $\hat{q}(\tau)$ is computed and the residuals and weights are recalculated. The features or modal displacements $\hat{q}(\tau)$ of the hyperplane approximately satisfying for all sensors, Eq. (0.5) appears within a few iterations.

The solution of Eq. (0.5) must be computed within each concentration step, c for the proposed CME estimator. To improve the convergence to the unbiased solution of $\hat{q}(\tau)$ sensors which are most outlying are completely removed. For the new group of sensors, M-estimation is used to find improved feature estimates. Selection of the influence function is critical to the CME estimator's performance.

For its gross outlier rejection capability, Tukey's bisquare function is chosen to compute the weights with the residuals of the data. The bisquare weighting function $w=\phi(x)/x$ is defined for the $k^{th}$ sensor as in Eq. (0.6), $$w_k^{(b,c)}\left(\frac{e_k^{(b,c)}}{\sigma_k^{(b,c)}}\right) = \begin{cases} \left(1 - \left(\frac{e_k^{(b,c)}}{\sigma_k^{(b,c)}}\right)^2\right)^2 & \left|\frac{e_k^{(b,c)}}{\sigma_k^{(b,c)}}\right| < h_0 \\ 0 & \text{otherwise} \end{cases} \qquad (0.39)$$

where $\sigma_k^{(b,c)}$ is the median absolute deviation (MAD), $h_0$ is a tuning constant, c is a concentration step, and b is an IRLS iteration count of the M-estimator. To achieve the maximum 95% asymptotic efficiency assuming residuals have a Gaussian distribution, it has been shown that a tuning constant of $h_0=4.685$ is required.

The MAD for the $k^{th}$ observation is calculated as in Eq. (0.7), $$\sigma_k^{(b,c)} = \text{MED}(|e_k^{(b,c)} - \text{MED}(e^{(b,c)})|)/0.6745 \qquad (0.40)$$

where the constant scaling 0.6745 is required to achieve a 37% Gaussian efficient consistent estimator of the standard absolute deviation [249]. While relatively low efficiency, the purpose of using MAD instead of using the true scale is to resist outliers. This it achieves remarkably well since the median is high breakdown.

However, The MAD is developed for symmetric distributions and does not address distribution skewness. This may be of concern since the explanatory data is multivariate skewed. Improvements of the MAD approximation for asymmetric long-tailed distributions are available if necessary. Given the weights, $w_k^{(b,c)}$ the linear system of equations is solved for $\hat{q}^{(b,c)}(\tau)$ given sensors in subset $S_g^c$ as in Eq. (0.8).

$$\sum_{k=1}^{S_g^c} w_k^{(b,c)}\left(\frac{e_k^{(b,c)}}{\sigma_k^{(b,c)}}\right)(s_k(x_C, y_C, z_C, \tau) - \qquad (0.41)$$

$$\Psi_k(x_C, y_C, z_C)\hat{q}^{(b,c)}(\tau))\Psi_k(x_C, y_C, z_C) = 0$$

The weighted least squares problem for the $c^{th}$ concentration step is solved in the same way as Eq. (0.5). Equations (0.6)-(0.8) are the primary feature estimator equations used within the concentration operator. They are iterated within any concentration step for a specified number of M-steps, $b_f$ resulting in $\hat{q}^{(b_f,c)}(\tau)$.

The purpose of concentration is to iteratively remove poor observations and asymptotically approach the true statistical center of the data distribution. The foregoing estimate is used to trim data through concentration before reapplying M-estimation. Utilizing sensors nearest to this centroid are assumed to give the best feature estimates. A best estimate of this center is the multivariate location T and dispersion V of the data. Sensors furthest from this centroid are downweighted in Eq. (0.8). However, it is proposed to not just down-weight sensors, but to completely remove gross outliers from consideration. The redescending M-estimator does in fact equate weights to 0 for gross outliers. Let the $k^{th}$ sensor data vector be defined as in Eq. (0.9), $$x_k \triangleq [\Psi_k(x_C, y_C, z_C) s_k(x_C, y_C, z_C, \tau)] \qquad (0.42)$$

Defining the data vector in this way ensures that outliers which depend on sensor readings shall not occur in the explanatory data. Only fixed outliers can occur in the explanatory data, which are to be addressed with a fixed trim criterion. From any sample sensor set $S_g^c \supseteq S$ a location vector (See Eq. (0.10))

$$T^{(b_f, c)} = \frac{1}{\sum w_k^{(b_f, c)}} \left( \sum_{k=1}^{S_g^c} w_k^{(b_f, c)} x_k \right) \qquad (0.43)$$

and dispersion matrix [See Eq. (0.11)]

$$V^{(b_f, c)} = \sum_{k=1}^{S_g^c} w_k^{(b_f, c)} x_k^T x_k \qquad (0.44)$$

are estimated in the $c^{th}$ concentration step. The weightings are the result of iterative M-steps over the subset of sensors $S_g^c$.

For the estimated location and variance, the squared Mahalanobis distance ($D^2$) is computed for every sensor data point k as in Eq. (0.12).

$$D^2(x_k) = x_k - T^{(b_f, c)})(V^{(b_f, c)})^{-1}(x_k - T^{(b_f, c)})^T \qquad (0.45)$$

This multivariate distance differs only from the Euclidean distance only in that it accounts for correlations between data points and is scale-invariant. If the population has a multivariate normal distribution, the $D^2$ is approximated and statistical cutoff points can be determined. The initial distribution of $D^2$ may be computed from the fixed modal matrix and time varying set of strain data with Gaussian noise. The maximum of the computed $D^2$ may be used as a upper bound for removing gross outliers. During each concentration step gross outliers are removed and the location and dispersion are re-estimated. The sample location and dispersion more closely resemble the population location and dispersion. Therefore the small outliers become more pronounced. As the $D^2(x_k)$ increases the sensor can be identified as an outlier and removed. Outliers missed by this trim procedure will more likely be down-weighted in the M-estimate [See Eq. (0.8)]. An approximation is used for the upper bound $D_{ub}^2$. It can be assumed that the distribution of $D^2(x_k)$, k=1 ... S is equal to or greater than the distribution of $D^2(\Psi_k(x_c, y_c, z_c))$, k=1 ... S if the sensor data has a Gaussian error distribution. Recall that $D^2$ is given in units of variance. This implies that the variance will increase with the additional DOF. Therefore it can be assumed that $D^2(\Psi_k(x_c, y_c, z_c)) + \theta(n_z) \geq D^2(x_k)$, k=1 ... S. Assuming the adjustment of $\theta(n_s)$ is due to the noise of the strain data the scalar upper bound is defined as in Eq. (0.13):

$$D_{ub}^2 \triangleq P_c \max_{k \in S} D^2(\Psi_k(x_C, y_C, z_C)) \qquad (0.46)$$

where $P_c$ is a tuning constant chosen to be slightly greater than 1. The tuning constant accounts for $\theta(n_s)$. By removing a portion $k \in S$ sensors with $D^2 - D_{ub}^2$ a new candidate group of sensors $S_g^{c+1}$ is found for the next concentration step, and consecutive M-steps. Simulation studies verify this approximation of the upper bound, $D_{ub}^2$ to be good for the strain mode matrix and strain data.

Robustness for multi-stage estimators tends to come from good starts (initial feature estimates). The first estimate of the system when $\tau$ is 0, (i.e. when the sensor system is first operational), is calculated with a non-robust least squares estimate. Since the first estimate is assumed to come from a working sensor system it is a robust estimate. The initial robust feature estimate $\hat{q}^{(0,0)}(0)$ is found by solving the least squares problem presented in Eq. (0.14), $$\sum_{k=1}^{S_g^c} (s_k(x_C, y_C, z_C, \tau) - \Psi_k(x_C, y_C, z_C) \hat{q}^{(0,0)}(0)) \Psi_k(x_C, y_C, z_C) = 0 \qquad (0.47)$$

where $S_g^0$ is the set all of the available working sensors.

During operation, a robust start is paramount. A significant advantage of a time based sensor system is that previous close estimates are available. The most robust start will therefore be the estimate from the previous time step. This is because the strain change is assumed to be small between discrete time steps. Thus, the robust starts between discrete time steps are implemented as in Eq. (0.15), $$\hat{q}^{(0,0)}(\tau) = \hat{q}^{(b_f, c_f)}(\tau - 1) \qquad (0.48)$$

where $b_f$ is the total number of M-steps chosen and $c_f$ is the total number of concentration steps.

The importance of starts carries over into the concentration steps themselves. In order to be high breakdown, each concentration step requires a robust start. Since the initial start $\hat{q}^{(0,0)}(0)$ is robust the final estimates at the end of each of the concentration steps: $\hat{q}^{(b_f,1)}(\tau)$, $\hat{q}^{(b_f,2)}(\tau)$, ... $\hat{q}^{(b_f,c_f-1)}(\tau)$ are robust [205].

This mean that the estimates of corresponding concentration steps are robust starts for respective next concentration steps: $\hat{q}^{(0,2)}(\tau)$, $\hat{q}^{(0,3)}(\tau)$, ... $\hat{q}^{(0,c_f)}(\tau)$. Therefore the following inheritance rule [See Eq. (0.16)] is used to generate robust starts between concentration steps:

$$\hat{q}^{(0,c+1)}(\tau) = \hat{q}^{(b_f, c_f)}(\tau) \qquad (0.48)$$

The full steps of the CME for any discrete time step are summarized in Algorithm 1 assuming that an initial OLS feature estimate has already been computed with Eq. (0.14) at time 0.

$\{s_k(x_c, y_c, z_c, \tau), \hat{q}^{(b_f, c_f)}(\tau-1)\} \rightarrow \hat{q}^{(b_f, c_f)}$      Algorithm 1

1) If c==0, compute $\hat{q}^{(0,0)}(\tau)$ with Eq. (0.15). Else compute $\hat{q}^{(0,c)}(\tau)$ with Eq. (0.16).
2) For b=0: $b_f$ Iteratively compute weights, $w_k^{(b_f, c)}$ with Eqs. (0.6)-(0.8) with $\hat{q}^{(0,c)}$
3) Compute location T (See Eq. (0.10)) and dispersion V (See Eq. (0.11)) with computed $w_k^{(b_f, c)}$
4) Compute $D^2(x_k)$, k=1 ... S, using Eq. (0.12) with computed T and S
5) Generate a new sensor set $S_g^{c-1}$ by trimming sensors below cutoff $D_{ub}^2$ described by Eq. (0.13).
6) If c<$c_f$, Go to Step 1. Else output $\hat{q}^{(b_f, c_f)}(\tau)$.

For each time step, the M-step iteration count $b_f$ may be initialized to be large, so that a robust redescending M-estimate initializes the CME. This improves the algorithm's stability during the concentration steps. Afterwards, single M-steps where $b_f$ is equal to 1, may be utilized. This has the effect of improving computational efficiency. The robust estimate from previous concentration steps are passed as robust starts to respective next concentration steps. Therefore, iterative application of the robustness inheritance concept guarantees robustness through all concentration operations.

It should now be apparent that the above-described system integrates modal filtering and distributed sensing, to monitor an array of sensors using a robust modal filter, in real time, immune to asymmetric sensor noise and sensor failures. The invention provides a practical, real-time approach to monitor the complex dynamics of a flexible aircraft using a robust modal filtering architecture and a computationally efficient concentration-based and M-estimator-based robust algorithm.

It should be understood that various changes may be made in the form, details, arrangement and proportions of the components. Such changes do not depart from the scope of the invention which comprises the matter shown and described herein and set forth in the appended claims.

The invention claimed is:

1. A computerized system for controlling aeroelastic behavior of an aircraft, comprising:
   a fiber-optic sensor array comprising a plurality of optical fibers oriented substantially parallel along a wing of said aircraft, each said optical fiber having a plurality of spaced fiber Bragg Gratings (FBGs);
   a processor in communication with said fiber-optic sensor array, said processor including a non-transitory computer-readable storage device storing a plurality of software modules including,
      a plant model comprising a finite element model of said aircraft,
      an assembler software module comprising a series of instructions for performing the steps of calculating a reduced modal matrix representing one of spatial or strain information at each FBG in said fiber-optic sensor array,
      a modal matrix software module for computing modal coordinates,
      a function estimator for estimating an optimal aerodynamic state from said modal coordinates; and
   a flight controller for estimating a performance optimization adjustment to said modal coordinates to maintain said optimal aerodynamic state.

2. The computerized system according to claim 1, wherein said modal matrix software module is a concentrated modal estimator (CME) configured to recursively estimate said modal coordinates from said FBG data that is closest to a statistical multivariate center of data.

3. The computerized system according to claim 1, wherein said flight controller is configured to compute required control surface deflections to produce an optimal drag configuration for said aircraft.

4. A system for dynamic aeroelastic control of an aircraft, comprising:
   a sensor array attached to said aircraft, said sensor array comprising a plurality of fiber Bragg Grating (FBG) sensors;
   a processor in communication with said sensor array, said processor including a non-transitory computer-readable storage device storing software comprising a series of instructions for performing the steps of,
   maintaining a finite element model (FEM) of said aircraft comprising a set of finite elements interconnected at a plurality of nodes,
   mapping a spatial position of each of said FBG sensors,
   monitoring strain at each of said FBG sensors in real time;
   calculating a sensor strain matrix representing linear axial strain at each of said FBG sensors from said modal shape deformation;
   removing rows of sensor strain matrix based on which sensors are used;
   applying a robust modal filter software module for modal coordinate transformation of said reduced sensor strain matrix into a strain-based modal matrix by projecting said reduced sensor strain matrix from physical space to modal space to define projected modal coordinates; and
   a function estimator for estimating the functional relationship of modal coordinates and aerodynamic efficiency; a controller for performance optimization adjustment with said modal coordinates to maintain said optimal aerodynamic state.

5. The system according to claim 4, wherein said aircraft comprises a wing and said is plurality of fiber Bragg Grating (FBG) sensors are spaced along a plurality of optical fibers running substantially parallel along said wing.

6. The system according to claim 4, wherein said FEM comprises a wing model.

7. The system according to claim 4, wherein said FEM comprises a model of the entire aircraft.

8. The system according to claim 4, wherein said step of monitoring deformation at each of said FBG sensors comprises measuring strain at each of said FBG sensors and estimating modal deformation from said measured strain.

9. The system according to claim 4, wherein said step of reducing said sensor strain matrix comprises weighting data.

10. The system according to claim 9, wherein said step of weighting data includes zero-weighting outlier data.

11. The system according to claim 4, wherein said controller comprises a flutter suppression module for minimizing aircraft flutter.

12. The system according to claim 4, wherein said controller comprises a drag minimization module for minimizing aircraft drag.

13. The system according to claim 4, wherein said controller comprises a performance optimization module for maximizing aircraft fuel efficiency.

14. A system for dynamic aeroelastic control of an aircraft, comprising:
   a sensor array attached to at least a portion of said aircraft;
   a processor in communication with said sensor array, said processor including a non-transitory computer-readable storage device;
   a plurality of software modules each comprising a series of instructions stored on the machine-readable storage device and embodying executable code run by the processor to perform a series of steps, said software modules further comprising,
   an assembler module for mapping a spatial position of each sensor in said sensor array, for monitoring deformation at each said sensor, and for calculating a sensor matrix representing spatial position and strain modes at each of said sensors in said array;
   a robust modal filter software module for modal coordinate transformation of said reduced sensor strain matrix into a strain-based modal matrix.

15. The system according to claim 14, wherein said software modules further comprise a finite element model (FEM) comprising a set of finite elements interconnected at a plurality of nodes.

16. The system according to claim 14, wherein said robust modal filter software module accomplishes modal coordinate transformation by projecting said sensor strain matrix from physical space to modal space to define projected modal coordinates.

17. The system according to claim 16, wherein said robust modal filter software module accomplishes modal coordinate transformation by the substeps of,
   projecting sensor data from said sensor array onto the nodes of said FEM using a robust regression operator to define a data matrix,
   reducing said data matric, and
   projecting said reduced data matrix from physical space to modal space to define projected modal coordinates.

18. The system according to claim 14, further comprising a function estimator for estimating an optimal aerodynamic state from said modal coordinates.

19. The system according to claim 18, further a control module for estimating a performance optimization measure to be imparted to a control surface to maintain said optimal aerodynamic state.

20. A method for dynamic aeroelastic control of an aircraft, comprising the steps of:
- providing said aircraft with a sensor array;
- maintaining a finite element model (FEM) of said aircraft comprising a set of finite elements interconnected at a plurality of nodes,
- mapping a spatial position of each of said FBG sensors,
- monitoring deformation at each of said FBG sensors from an un-deflected position in real time;
- calculating a sensor strain matrix representing spatial position and strain modes at each of said FBG sensors from said deformation;
- reducing said sensor strain matrix;
- applying a robust modal filter software module for modal coordinate transformation of said reduced sensor strain matrix into a strain-based modal matrix by projecting said reduced sensor strain matrix from physical space to modal space to define projected modal coordinates;
- estimating an optimal aerodynamic state of said aircraft from said projected modal coordinates; and
- estimating a performance optimization adjustment to said modal coordinates to maintain said optimal aerodynamic state.

* * * * *